United States Patent
Polier et al.

(10) Patent No.: US 7,820,128 B2
(45) Date of Patent: Oct. 26, 2010

(54) PRODUCTION OF CU/ZN/A1 CATALYSTS VIA THE FORMATE ROUTE

(75) Inventors: Siegfried Polier, Bruckmuhl (DE); Martin Hieke, Bruckmuhl (DE); Dieter Hinze, Kolbermoor (DE)

(73) Assignee: Sud-Chemie AG, Munich (DE)

( * ) Notice: Subject to any disclaimer, the term of this patent is extended or adjusted under 35 U.S.C. 154(b) by 295 days.

(21) Appl. No.: 11/911,581

(22) PCT Filed: May 2, 2006

(86) PCT No.: PCT/EP2006/004091

§ 371 (c)(1),
(2), (4) Date: Oct. 15, 2007

(87) PCT Pub. No.: WO2006/117190

PCT Pub. Date: Nov. 9, 2006

(65) Prior Publication Data

US 2009/0048355 A1   Feb. 19, 2009

(30) Foreign Application Priority Data

May 3, 2005   (DE) .................. 10 2005 020 630

(51) Int. Cl.
*C01B 31/20* (2006.01)
*C01B 3/16* (2006.01)
*C01B 3/22* (2006.01)
*B01J 23/80* (2006.01)
*C07C 27/06* (2006.01)

(52) U.S. Cl. ............ 423/437.2; 423/648.1; 423/656; 502/342; 518/713

(58) Field of Classification Search ........ 158/711, 158/713; 502/341, 342, 346, 506, 512; 423/42, 423/43, 101–106, 115–117, 600, 594.14, 423/437.2, 656, 648.1; 518/713
See application file for complete search history.

(56) References Cited

U.S. PATENT DOCUMENTS

| 3,850,850 A |   | 11/1974 | Collins |  |
|---|---|---|---|---|
| 3,923,694 A |   | 12/1975 | Cornthwaite |  |
| 4,279,781 A |   | 7/1981 | Dienes |  |
| 4,508,641 A | * | 4/1985 | Hanulik ............... | 588/3 |
| 4,535,071 A |   | 8/1985 | Schneider |  |
| 4,598,061 A | * | 7/1986 | Schneider et al. ........... | 502/303 |
| 5,019,547 A | * | 5/1991 | Chaumette et al. .......... | 502/342 |
| 5,254,520 A |   | 10/1993 | Sofianos |  |
| 5,631,302 A |   | 5/1997 | Konig |  |
| 5,871,647 A | * | 2/1999 | Lord .......................... | 210/615 |
| 5,990,040 A | * | 11/1999 | Hu et al. ..................... | 502/342 |
| 6,623,646 B2 | * | 9/2003 | Bryant et al. ............... | 210/717 |
| 2005/0080148 A1 |   | 4/2005 | Ladebeck |  |
| 2009/0325794 A1 | * | 12/2009 | Wolk et al. ................ | 502/324 |

FOREIGN PATENT DOCUMENTS

| EP | 431589 A2 * | 6/1991 |
|---|---|---|
| EP | 0482753 | 4/1992 |
| GB | 1286970 | 8/1972 |
| GB | 1366367 | 9/1974 |
| JP | 7008799 | 1/1995 |
| JP | 2001321679 | 11/2001 |

OTHER PUBLICATIONS

B.Denise et al. "Oxide-supported copper catalysts prepared from copper formate: differences in behaviour in methanol synthesis from CO/H2 and CO2/H2 mixtures" , 1986, Elsevier Science Publishers B.(Applied catalysis), vol. 28, p. 235-239.*
Zhang et al. "Methanol synthesis on Cu-Zn-Al and Cu-Zn-Al-Mn catalysts". 1997, Applied Catalysis, vol. 165, p. 411-417.*
Office Action dated May 12, 2009 with respect to the potentially related U.S. Appl. No. 10/497,865.
Office Action dated Mar. 21, 2008 with respect to U.S. Appl. No. 10/497,865.
Response filed Jun. 20, 2008 with respect to U.S. Appl. No. 10/497,865.
Final Office Action dated Oct. 1, 2008 with respect to U.S. Appl. No. 10/497,865.
Response filed Mar. 2, 2009 with respect to Final Office Action dated Oct. 1, 2008 in U.S. Appl. No. 10/497,865.
English translation of International Preliminary Report on Patentability pertaining to international application No. PCT/EP2006/004091, filed in the U.S. under U.S. Appl. No. 11/911,581. This application may contain information material to the patentability of the current application.

* cited by examiner

*Primary Examiner*—Wayne Langel
*Assistant Examiner*—Syed Iqbal
(74) *Attorney, Agent, or Firm*—Scott R. Cox

(57) ABSTRACT

The invention relates to a process for preparing Cu/Zn/Al catalysts. In this process, the metals are used in the form of their formates and are precipitated in a suitable form. Suitable precipitants are, for example, alkali metal carbonates. The invention further relates to a catalyst as can be obtained by the process according to the invention and to its use.

32 Claims, No Drawings

PRODUCTION OF CU/ZN/A1 CATALYSTS VIA THE FORMATE ROUTE

The invention relates to a process for preparing Cu/Zn/Al catalysts, to a catalyst which can be obtained by the process, and to its use for methanol synthesis and the reformation of methanol and the low-temperature conversion of carbon monoxide.

Cu/Zn/Al catalysts which catalyze the conversion of CO, $CO_2$ and $H_2$ to methanol have been known for some time. The atomic ratios between copper and zinc can vary in these known catalysts, except that copper is generally present in excess. Moreover, part of the zinc component can be replaced by calcium, magnesium and/or manganese. The aluminum oxide used as a thermally stabilizing substance can also be replaced partly by chromium oxide.

For example, DE 1 965 007 discloses a catalyst for low-temperature methanol synthesis. For the preparation of the catalyst, the corresponding basic carbonates are first precipitated from a solution of suitable zinc and copper salts by adding alkali metal carbonates. The basic carbonates are removed from the aqueous phase, dried and calcined in order to obtain the corresponding oxides. The zinc oxides and copper oxides are subsequently mixed with aluminum oxide to prepare a suspension of the oxides which contains not more than 20% solids. This is subsequently homogenized, the homogenization being performed until the dispersed oxides do not settle out over the course of 2 hours. After the homogenization, the mixture is dried, tableted and calcined. In order to convert the oxidic form to the catalyst, it is then reduced in a hydrogen stream.

DE 2 302 658 A discloses a process for preparing a precursor for a catalyst which can be used for methanol synthesis. To prepare the catalyst precursor, a first precipitate which comprises a divalent metal, for example zinc, and a trivalent metal, for example aluminum, is first prepared in the form of a compound which can be decomposed thermally to the corresponding oxides. Suitable compounds are, for example, carbonates or bicarbonates. In addition, a second precipitate which comprises copper compounds which can be decomposed thermally to oxides is prepared. The two precipitates are mixed. This is followed by the customary stages of drying and calcination in order to obtain the oxides from the metal compounds and possibly to bring about the formation of a spinel structure. The solid is then tableted. In order to convert the precursor to an active catalyst, the tablets are reduced in a hydrogen stream.

DE 2 056 612 A describes a process for preparing methanol, the conversion being effected over a catalyst which comprises zinc, copper and aluminum. The catalyst belongs to a mixed crystal series of the formula $(Cu_xZn_y)Al_2(OH)_{16}.CO_3.4H_2O$ in which x and y can assume numerical values from 0.5 to 5.5, and the sum of x and y is equal to 6. The mixed crystal compound is precipitated from an aqueous solution which comprises copper, zinc and aluminum salts by adding alkali metal carbonates, alkali metal bicarbonates or mixtures thereof. The atomic ratio of the sum of the divalent metals copper and zinc to the trivalent aluminum in the mixed crystal series is constant and is 6:2. For the preparation, copper, zinc and aluminum are dissolved in water in the form of suitable salts, preferably of the nitrates, in a quantitative ratio which corresponds to the desired composition of the catalyst. This solution is heated to temperatures of from 50 to 100° C., preferably from 70 to 100° C., and treated with an aqueous solution of a precipitant, for example of an alkali metal carbonate, at an appropriate temperature. The precipitate formed is filtered off, washed and dried. The dried compound is calcined at temperatures in the range from 200 to 500° C. over from 12 to 24 h. The calcined product is shaped to tablets and then converted to the active form of the catalyst by reduction in a hydrogen stream.

U.S. Pat. No. 4,279,781 describes a catalyst for methanol synthesis, which comprises copper oxide and zinc oxide and also a metal oxide for the thermal stabilization, for example aluminum oxide. The ratio of copper oxide and zinc oxide is, calculated as the weight of the metals, from 2:1 to 3.5:1. The catalyst is prepared by coprecipitation of soluble zinc, copper and aluminum salts, for example of the nitrates. This achieves intimate mixing of the catalyst constituents. In order to obtain the active form, the catalyst precursor is reduced in a hydrogen stream.

EP 0 125 689 A2 discloses a catalyst for methanol synthesis, which comprises, as catalytically active substances, copper oxide and zinc oxide and, as a thermally stabilizing substance, aluminum oxide. The catalyst features a particular pore radius distribution, the proportion of the pores having a diameter of from 20 to 75 Å (mesopores) being at least 20% and the proportion of the pores having a diameter of more than 75 Å (macropores) being at most 80%. The desired pore radius distribution can be achieved by using colloidally distributed aluminum oxide or hydroxide in the preparation of the catalyst. For the preparation of these catalysts, the catalytically active copper oxide-zinc oxide component is precipitated from aqueous solutions of the corresponding salts, for example the nitrates, sulfates, chlorides, acetates, with alkaline substances in the presence of a colloidally distributed aluminum oxide or hydroxide. The precipitation product can subsequently be dried, calcined, compressed to shaped bodies and optionally reduced.

EP 0 152 809 A2 discloses a catalyst for synthesizing alcohol mixtures comprising methanol and higher alcohols, said catalyst comprising copper oxide and zinc oxide in the form of an oxidic precursor which can be converted by a reduction of at least a portion of the copper oxide to a catalytically active component, and also aluminum oxide as a thermally stabilizing substance, and at least one alkali metal carbonate or alkali metal oxide. The oxidic precursor has a proportion of pores having a diameter between 14 and 7.5 nm of from 20 to 70% of the total volume. The alkali metal content is from 13 to $130\times10^{-6}$ gram atom of alkali metal per gram of the oxidic precursor. The aluminum oxide component was obtained from a colloidally distributed aluminum hydroxide. For the preparation of the catalyst, generally solutions of the nitrates of copper and zinc are used, and the precipitation is preferably performed with an aqueous $K_2CO_3$ solution. The concentration of the solution is preferably from 5 to 20% by weight. Instead of the nitrates, it is also possible to proceed from the corresponding metal formates or acetates. The precipitation can also be performed with the aid of a potassium hydrogen carbonate solution. The precipitation can be performed batchwise or continuously. Preference is given to performing the precipitation by continuously combining the solution of the nitrates of copper and zinc which comprises the aluminum hydroxide distributed in colloidal form with aqueous $K_2CO_3$ solution. After the precipitation, the washed precipitate of the catalyst is calcined and alkalized by treatment with a solution of an alkali metal compound. The alkalized catalyst precursors are, after drying, compressed to shaped bodies in a manner known per se, for which lubricants such as graphite can be added. In order to convert the catalyst precursor to an active form, it is reduced with hydrogen.

WO 03/053569 A1 discloses a catalyst for methanol synthesis, which comprises copper oxide and zinc oxide as catalytically active substances and aluminum oxide as a thermally stabilizing substance. To prepare the catalyst, the corresponding hydroxycarbonates or hydroxides are precipitated from a solution which comprises the Cu and Zn salts and a portion of the Al salts with an alkali metal carbonate or alkali metal aluminate solution. Either the solution of the Cu and Zn salts or the alkali metal carbonate or alkali metal aluminate solution comprises an aluminum hydroxide sol. The precipitate obtained is removed from the precipitation solution, washed, dried and optionally calcined. In the preparation of the catalyst, the starting materials are preferably the copper and zinc nitrates, which are preferably precipitated with sodium carbonate or sodium aluminate.

JP 2000-144779 describes a copper-zinc catalyst for the reaction of carbon monoxide and water to give carbon dioxide and water, which is prepared by mixing a solution which comprises copper formate and zinc formate with an aqueous solution of an alkali metal material. The resulting precipitate is subsequently filtered, washed, dried and calcined. The calcined solid is slurried by adding water and applied to the surface of a honeycomb carrier. The binder used may be aluminum oxide sol or zirconium oxide sol. These are added to the slurry of the calcined precipitate. The aluminum oxide is therefore not distributed homogeneously in the catalyst but rather arranged merely between the catalyst particles. It thus merely has the task of acting as a binder between the copper- and zinc-containing catalyst particles and the honeycomb carrier, and is not an active part of the catalyst.

For the preparation of Cu/Zn/Al catalysts for the methanol synthesis, copper nitrates and zinc nitrates are usually used in industrial processes owing to their good water solubility. In the precipitation, wastewaters which comprise large amounts of sodium nitrate are therefore obtained. On introduction into surface waters, this would lead to overfertilization. Before introduction into surface waters, the content of water-soluble nitrogen in the wastewater obtained in the preparation of the methanol synthesis catalyst must therefore be reduced drastically.

It is therefore an object of the invention to provide a process for preparing Cu/Zn/Al catalysts which firstly enables a significant reduction in the salt burden, especially of alkali metal nitrates, in the wastewater, and which secondly provides catalysts for the methanol synthesis which have at least a comparable activity to a catalyst prepared from metal nitrates.

This object is achieved by a process having the features of claim 1. Advantageous embodiments of the process form the subject matter of the dependent claims.

In the process according to the invention for preparing Cu/Zn/Al catalysts, a first aqueous solution which comprises at least copper formate and zinc formate is first prepared. In addition, a second solution which comprises a precipitant is prepared. A precipitant is understood to be a reagent which directly or indirectly provides ions, for example hydroxyl ions and/or carbonate ions, with which the metals, especially copper, zinc and aluminum, can be precipitated. The first solution and/or the second solution comprises an aluminum hydroxide sol/gel mixture.

An aluminum hydroxide sol is understood to mean a finely dispersed distribution of aluminum hydroxide in water, in which polyacids have already formed by condensation of aluminum hydroxide, but still no particles are perceptible with the naked eye in the aqueous phase, i.e. a clear solution is present. An aluminum hydroxide gel is understood to mean a dispersion of aluminum hydroxide in water where relatively large agglomerates of polyacids have already formed, such that particles can be perceived even with the naked eye, for example as opacity of the aqueous phase.

In a precipitation step, the first solution and the second solution are combined to obtain a precipitate. The precipitate is removed from the aqueous phase, and the aqueous phase forms wastewater which is sent to a workup.

The precipitate is washed until it has an alkali metal content of less than 500 ppm based on the catalyst calcined at 600° C. Subsequently, the precipitate is dried, optionally calcined and ground.

In the process according to the invention, no nitrate-containing wastewaters are obtained. As a result of the use of copper formate and zinc formate as water-soluble copper and zinc salts, the wastewater comprises formate ions which can be worked up in a simple manner. Through the use of formates, the contamination of the wastewater with organic material is kept relatively low. This is an advantage over the use of higher carboxylic acids, such as acetic acid, since they increase the organic contamination in the wastewater through the greater number of C—H bonds. As a further advantage, formic acid, which is required for the preparation of the copper formates and zinc formates, can be prepared inexpensively, so that the process according to the invention is also advantageous from cost aspects.

For the process according to the invention, it is essential that at least a portion of the aluminum is introduced into the precipitation solution in the form of an aluminum hydroxide sol and another portion as an aluminum hydroxide gel. When the addition of the aluminum hydroxide sol/gel mixture into the solution of the metal salts is dispensed with, the weight-time yield falls (WTY, [kg of methanol/{kg of catalyst× hour}]).

After the removal, the precipitate is washed carefully, such that its alkali metal content, based on the oxidic catalyst calcined at 600° C., falls to values of less than 500 ppm, preferably less than 400 ppm, especially to values in the range from 100 to 300 ppm. The washing water obtained can be combined with the formate-containing wastewater and optionally worked up. After the washing, drying and optionally calcining, the oxidic form of the catalyst still has a residual formate content of less than 5% by weight, preferably from 0.5 to 4% by weight, especially preferably 1-2% by weight. The formate content can be determined, for example, by oxidative titration or by quantitative chromatographic processes, for example HPLC.

As well as the copper formate and the zinc formate, the first aqueous solution may also comprise customary promoters, for example calcium, magnesium, manganese, cerium, lanthanum, and also ruthenium or palladium. As well as the promoters mentioned, it is also possible for other promoters to be used. The promoters are preferably likewise introduced in the form of their formates, preferably into the first aqueous solution. Their proportion in the oxidic form of the catalyst is, calculated as the oxide, preferably less than 10% by weight, especially less than 5% by weight. When noble metals, such as ruthenium or palladium, are used as promoters, they are present preferably in amounts of less than 1% by weight.

As already mentioned, in the process according to the invention, the first and/or the second solution comprises an aluminum hydroxide sol/gel mixture. The starting material used for the aluminum hydroxide sol/gel may, for example, be a commercially available product. The aluminum hydroxide sol/gel mixture can, though, also be obtained by adding a little ammonium hydroxide to a dilute aluminum salt solution while avoiding heating in order to delay the conversion to coarsely dispersed hydroxo derivatives. In a further variant, a small amount of acid can be added to an alkali metal aluminate solution to form the aluminum hydroxide sol/gel. The aluminum hydroxide sol/gel is preferably present in the first aqueous solution. The conversion products formed from the aluminum hydroxide sol/gel serve both as supports and as thermally stabilizing substances. Without being bound to this theory, the inventors suspect that the aluminum hydroxide sol/gel mixture, in the course of heating, forms a three-dimensional network in whose gaps the copper crystals which belong to the active species and are present after the reduction are arranged. As a result, further growth of the copper crystals during the methanol synthesis becomes more difficult, which increases the stability of the catalyst and its lifetime in industrial processes.

Zinc oxide is assumed firstly to exert an important influence on the formation of the active species and secondly to contribute to the stability of the catalyst through its partially needlelike structure. Moreover, the zinc oxide acts as a scavenger of poisons by reacting with any sulfur compounds which occur.

The oxides of calcium, of magnesium, of manganese, of cerium and of lanthanum which may be present as promoters likewise have a stabilizing action.

The first solution, which comprises a mixture of different metal salts, is preferably prepared by
preparing an aqueous copper formate solution by dissolving a copper salt without residue by adding formic acid,
preparing an aqueous dispersion or solution of a zinc salt,
preparing an aqueous aluminum salt solution, and
combining the copper formate solution, the dispersion or solution of the zinc salt and the aluminum salt solution.

When the Cu/Zn/Al catalyst is still to be modified by promoters, they may, for example, be added to the first solution. The promoters may be added in the form of suitable salts, for example as carbonates, oxides or hydroxides. In principle, these salts may be added at any time, i.e. to the copper formate solution, to the dispersion or solution of the zinc salt, or else after combination of the copper formate solution and of the dispersion or solution of the zinc salt. Particularly expensive promoters, such as noble metals, are preferably added to the suspension in a later process step, for example before the spray drying, or sprayed onto the dry powder in ultrafinely distributed form after the spray-drying.

In the preparation of the copper-zinc formate solution, preference is given to adding sufficient formic acid that, based on the amount of copper salt and zinc salt used, taking account of the stoichiometry, the formic acid is present in an excess of at least 10 mol %, preferably from 10 to 20 mol %, especially preferably from 14 to 16 mol %. After the addition of the formic acid, the pH of the copper formate solution is preferably less than 3, preferably less than 2.5.

In a preferred process version, the solution or dispersion of the zinc salt is combined with the copper formate solution. After the copper formate solution or dispersion and the zinc salt solution or dispersion have been combined, both the copper and the zinc are present in the form of their formates in solution. The resulting solution preferably has a pH in the range from 3.0 to 4.0, especially preferably from 3.5 to 3.7. Subsequently, the aluminum salt solution is added to the copper/zinc solution.

The aluminum salt solution is preferably added to the copper/zinc solution in several portions. In this case, at least one first portion of the aluminum salt solution is prepared by dissolving at least a first portion of the aluminum salt in water with addition of formic acid.

In the preparation of the first portion of the aluminum salt solution, the procedure is preferably first to dissolve sodium aluminate, for example, in water and then to add sufficient formic acid that the pH is in the range of less than 5, preferably from 4.5 to 2, especially from 4 to 3. Preferably sufficient formic acid is added to obtain a clear solution.

Preference is given to preparing a second portion of the aluminum salt solution by dissolving a second portion of the aluminum salt in water. In this case, no formic acid is added to the second portion of the aluminum salt solution. To complete the first solution, which comprises the mixture of all metal salts before the precipitation, the first portion of the aluminum salt solution and the second portion of the aluminum salt solution, preferably offset in time, are preferably added to the aqueous copper/zinc solution.

The second portion of the aluminum salt solution is prepared, for example, by dissolving $NaAlO_2$ in water. The pH of the aqueous $NaAlO_2$ solution is, depending on the alkali excess in the reactant, in the range from 11 to 14, preferably from 12 to 13.

The proportions of the first and second portion of the aluminum salt solution may, based on the aluminum content, be selected within the range from 0:100 to 100:0, preferably from 1:99 to 99:1, more preferably from 30:70 to 70:30 and especially preferably at about 50:50.

The aluminum salt solutions are prepared preferably at temperatures of less than 40° C., especially preferably less than 30° C. This temperature should also not be exceeded when the aluminum salt solution is added to the copper/zinc solution or to the copper formate solution or to the dispersion or solution of the zinc salt. In this way, the formation of coarsely dispersed polymeric aluminum compounds is suppressed. Coarsely dispersed polymeric aluminum compounds are understood to mean complex aluminum hydroxo compounds which form particles which are visible to the eye and sink relatively rapidly. Preference is therefore given to preparing the solutions in a tank which is equipped with an appropriate cooling device.

Aluminum salts which can be used in a suitable manner in the process according to the invention are, for example, aluminum di- and triformate, $Al(NO_3)_3$ hydrates or $NaAlO_2$. The aluminum salt solutions preferably have an aluminum concentration in the range from about 0.4 to about 1.1 mol/l, especially preferably from about 0.9 to 1.1 mol/l. The upper value of the range specified is determined by the solubility limit of the aluminum salt, while the lower limit arises from economic considerations.

The copper salts used are preferably those salts whose anions are oxides, hydroxides and carbonates or their derivatives obtained by reduction, and can no longer be detected separately by means of distinguishable elements in the first solution or in the oxidic form of the catalyst. The copper salt is preferably selected from CuO, $Cu(OH)_2$ and $Cu(OH)_2 \cdot CuCO_3$.

The zinc salt selected is preferably likewise a zinc compound whose anion is not disruptive in the first solution or in the oxidic precursor of the catalyst, and is preferably not detectable as a distinguishable element. The zinc salt selected is preferably ZnO.

The concentration of the copper formate solution is preferably selected such that, after the copper formate solution and zinc salt solution or dispersion have been combined, the concentration of the copper is set within a range of from about 0.1 to about 0.5 mol/l, especially preferably from 0.3 to about 0.5 mol/l. The upper limit is determined by the solubility limit of the copper salt, while the lower limit arises from economic considerations, since the processing of dilute solutions gives rise to relatively large volumes, which influences, for example, the dimensioning of the apparatus in which the process according to the invention is performed.

The concentration of the zinc salt is preferably selected such that, after the copper formate solution and zinc salt solution or dispersion have been combined, the concentration of the zinc is preferably within the range from about 0.1 to about 0.2 mol/l, preferably from 0.15 to about 0.2 mol/l. The upper limit arises here too from the solubility of the zinc salt, and the lower limit from economic considerations.

The aluminum salt solution is preferably added to the copper/zinc solution. The pH of the first solution, which preferably comprises the total amount of Cu, Zn and Al, is then preferably adjusted to a value in the range from 4.0 to 5.0, more preferably from 4.2 to 4.4.

The precipitation reagent used is preferably an alkali metal base. The alkali metal bases used are preferably alkali metal carbonates, alkali metal hydrogencarbonates or alkali metal aluminates. The alkali metal used is preferably sodium. When, for example, a sodium carbonate solution is used as the precipitation reagent, the sodium carbonate solution preferably has a concentration of from 80 g/l to 200 g/l, preferably from 170 to 180 g/l.

In a further embodiment of the process according to the invention, the precipitation reagent used is hydrogen peroxide. The hydrogen peroxide is added to the first solution or dispersion, which comprises copper, zinc and aluminum in the form of their formates or hydroxoformates. The hydrogen peroxide oxidizes the formate to carbonate, so that the metals are precipitated in the form of their hydroxocarbonates, carbonates or hydroxides. In the oxidation of the formate anion, first the hydrogencarbonate anion and then the carbonate anion are formed with rising pH. The metal ions used are precipitated as hydroxocarbonates in a sequential precipitation in the series of Al—Cu—Zn. The use of a carbonate-containing alkali metal solution can thus be dispensed with. In addition to hydrogen peroxide, it is also possible to use other suitable oxidizing agents, for example ozone.

To prepare the oxidic catalyst precursor, first and second solution are first combined to obtain a precipitate. The precipitation is preferably performed in such a way that, during the precipitation, a pH in the range from 3.5 to 7.5, preferably from 6.0 to 7.0, especially preferably 6.5±0.1, is maintained.

The temperature during the precipitation is preferably kept within a range from 25 to 95° C., especially preferably from 50 to 75° C.

After the mixing, the precipitate formed is preferably aged. To this end, the suspension obtained in the mixing of first and second solution can, for example, be transferred to an aging vessel in which the suspension can be moved, for example, with a suitable stirrer.

The aging is performed preferably over a period of from 10 minutes to 10 hours, especially preferably from 1 to 5 hours.

During the aging, the suspension is preferably heated, the aging being effected especially at a temperature of more than 60° C., especially preferably within the range from 65 to 80° C.

The combination of first and second solution is preferably performed in such a way that the solutions are introduced in parallel into a mixing vessel and mixed there. Rapid mixing is effected therein, for example by means of a suitable stirrer.

However, preference is given to performing the precipitation as a continuous precipitation. To this end, an appropriately dimensioned mixing vessel is provided, into which first and second solution are fed continuously and the resulting mixture is removed continuously. The volume of the mixing vessel is preferably selected such that first and second solution can be fed continuously into the mixing vessel and the mixture can be removed continuously, the residence time of the mixture being preferably within the range from about 0.1 second to 10 minutes, more preferably from about 1 to 120 seconds, especially preferably from 1 to 20 seconds.

The residence time of the mixture in the mixing vessel depends greatly upon the dimensioning of the mixing vessel and the flow rate. The dimensioning of the mixing vessel and the feed and removal rates of the solutions or suspension can be selected in a suitable manner correspondingly by the person skilled in the art.

After the precipitation and any aging step performed, the precipitate is removed from the aqueous phase, for which customary processes can be used, for example a filtration. The precipitate is subsequently washed and dried. The precipitate is preferably calcined after drying. Depending on the process used, the calcination is effected at temperatures of preferably from 140° C. to 1000° C., especially preferably from 170° C. to 350° C., for a period of at least 0.1 second, preferably at least 4 minutes, more preferably from 20 minutes to 8 hours, especially preferably from 30 minutes to 4 hours. Depending on the calcination conditions selected, the formate remaining in the filtercake, in the course of calcining, is largely eliminated oxidatively under air or by an intramolecular redox reaction under inert gas. In the latter case, the $Cu(HCO_2)_2 \cdot H_2O$ is suspected to be decomposed first to $H_2$ and $CuC_2O_2$. The copper oxalate then reacts further to give $CO_2$ and elemental copper. The calcination can be performed in customary apparatus. In an industrial manufacture, owing to the better heat transfer, both pulsation reactors and fluidized bed reactors, such as the commercially preferred rotary tube ovens, are used. Pulsation dryers enable very short drying times in the region of less than 1 second, generally within the range from 0.1 second to 4 minutes, and very high temperatures of up to 1000° C. may be employed.

The calcined powder can optionally be ground and then processed by means of customary tools, for example to tablets or extrudates. However, it is also possible to slurry the powder, to grind it to a very fine particle size and to coat suitable support bodies, for example honeycombs, with the resulting suspension. It is possible here to employ customary processes. The particle size is suitably adjusted such that the mean particle size $D_{50}$ is in the range from 10 nm to 10 μm, especially preferably from 100 nm to 5 μm. The mean particle size can be determined, for example, by laser light scattering. Suitable catalysts can be prepared, for example, with particle sizes in which the $D_{50}$ value is in the range of about 2-3 μm.

A particular advantage of the process according to the invention is that the formate-containing wastewater obtained after the removal of the precipitate can be worked up by comparatively simple means. For this purpose, the formate-containing wastewater is preferably subjected to an oxidative treatment, which oxidizes the formate ions in the aqueous solution, depending on the pH, essentially to carbonate, hydrogencarbonate, carbon dioxide and water. The content in the wastewater of formate, for example in the form of sodium formate, in an industrial implementation of the process according to the invention, is typically in the range from 0.2 to 1.5 mol/l, especially preferably from 0.8 to 1.0 mol/l, although it is also possible for higher or lower formate concentrations to be present. The oxidative treatment of the wastewater allows the formate concentration to be lowered to values of less than 0.1 mol/l, preferably from 0.01 to 0.075 mol/l, especially preferably from 0.02 to 0.04 mol/l. This corresponds to a lowering in the amount of formate present in the wastewater by more than 95%.

In a preferred embodiment, hydrogen peroxide is added to the formate-containing wastewater for oxidative treatment. The hydrogen peroxide is preferably added to the formate-containing wastewater in the form of a solution whose hydrogen peroxide concentration is in the range from about 9 to 20 mol/l (up to approx. 60% by weight). In the case that the relevant transport regulations are complied with, the concentration of the hydrogen peroxide solution used can be increased up to above 90% by weight. Preference is given to adding the hydrogen peroxide in excess, in which case the amount added, based on the formate present in the wastewater, is selected within the range from 160 to 200 mol %, especially preferably from 160 to 170 mol %. As well as hydrogen peroxide, it is also possible to use other oxidizing agents, for example ozone or sodium hypochlorite solution. In the selection of the oxidizing agents, for example, production costs and environmental legislation play a role. Depending on the legal limits and the further purification stages available, it is under some circumstances not necessary to oxidize the entire amount of the formate ions. It may actually be sufficient to considerably reduce the concentration of the formate ions by a chemical oxidative treatment and to feed the wastewater thus treated optionally, for example, to a biological clarification stage.

The treatment of the formate-containing wastewater with hydrogen peroxide is performed preferably at from 20 to 95° C., especially preferably at from 50 to 80° C., within a pH range of 4-8, especially preferably from 5.0 to 6.5.

In one embodiment of the process according to the invention, the oxidative treatment of the formate-containing wastewater is effected actually before the removal of the precipitate. To this end, after the aging step, for example, a suitable amount of hydrogen peroxide can be added to the suspension and the precipitate can be removed only after the substantial oxidative degradation of the formate ions. Alternatively, in the course of the process with time, the hydrogen peroxide solution can also be added actually to the Cu-, Zn-, Al-containing formate solution, in which case the precipitation reagent, carbonate ions, is generated from formate ions by oxidation.

The oxidative workup of the wastewater by adding a suitable oxidizing agent, such as hydrogen peroxide, is quite simple to perform in apparatus terms and also enables the treatment of wastewaters which have a relatively high concentration of formate ions. However, it is also possible that the oxidative treatment is effected solely by a biological treatment of the formate-containing wastewater. If appropriate, the formate-containing wastewater can be diluted to a suitable concentration for this purpose.

The oxidative treatment of the formate-containing wastewater is preferably performed in such a way that the formate concentration in the wastewater after the oxidative treatment is less than 0.1% by weight.

When the Cu/Zn/Al catalyst obtained using the formates is compared with catalysts which have been prepared starting from the nitrates, the catalyst obtained by the process according to the invention exhibits a better to comparable activity and a comparable selectivity. The long-term stability of the catalyst prepared using the formates, which has been determined in the methanol synthesis test at 250° C., is also somewhat better than or at least comparable with the stability of a catalyst which has been prepared starting from the metal nitrates. The invention therefore also provides a catalyst which can be prepared by the above-described process.

The inventive catalyst contains, in its oxidic form, less than 5% by weight, preferably between 0.5 and 4% by weight, especially preferably between 1 and 2% by weight of formate, calculated as formic acid. Gentle calcination allows preservation of the formate structure which, according to the lock-and-key principle which is frequently encountered in catalysis, can play an important role for the attainment of a high activity. A gentle calcination at about 170° C. for 4 minutes forms a catalyst which exhibits a very high activity at 250° C.

The inventive catalyst features a high mesopore volume. The proportion of mesopores having a radius of from 3.75 to 7.0 nm in the total pore volume is preferably more than 30%, preferably from 30 to 80%. The total pore volume includes the volume of the pores having a radius of from 3.75 to 7500 nm. The pore volume can be determined by the mercury intrusion method. The total pore volume, determined on 6×4 mm tablets, is preferably 100 mm$^3$/g-700 mm$^3$/g, preferably 250 mm$^3$/g-450 mm$^3$/g.

The proportion of the copper, calculated as CuO and based on the weight of the oxidic catalyst form, taking account of the ignition loss at 600° C., is selected preferably between 55 and 69 by weight, especially preferably 60 and 63 by weight.

The proportion of the zinc, calculated as ZnO and based on the weight of the oxidic catalyst form, taking account of the ignition loss at 600° C., is selected preferably between 20 and 33% by weight, especially preferably between 25 and 31% by weight.

The proportion of aluminum, calculated as $Al_2O_3$ and based on the weight of the oxidic catalyst form, is selected preferably between 5 and 20% by weight, especially preferably between 8 and 11% by weight.

The percentages for the proportions of the copper, zinc and aluminum are based on a catalyst calcined at 600° C. for three hours.

The inventive catalyst also has, in the oxidic form, an alkali metal ion content, especially sodium ion content, of preferably less than 500 ppm, especially preferably less than 300 ppm, especially from 100 ppm to 300 ppm.

In its oxidic form, the inventive catalyst preferably has a specific surface area of more than 90 m$^2$/g, especially preferably more than 100 m$^2$/g.

The inventive catalyst can in principle be molded as shaped bodies with any shape. For example, it can be configured in the form of rings, 3-20 hole shaped bodies, tablets with a smooth or undulating surface, or honeycombs. The dimensioning of the shaped bodies corresponds to the customary values. For the preparation of the shaped bodies, the pulverulent catalyst, optionally with addition of a lubricant, such as graphite, is compressed, for example to tablets of, for example, 6×4 mm.

Before use, the catalyst is converted from the oxidic form to the active form. To this end, the copper oxide is at least partly reduced to elemental copper. For this purpose, the oxidic form of the inventive catalyst is preferably reduced in a hydrogen stream. The activation can be effected directly within the synthesis reactor and is preferably done by reducing first with the aid of an inert gas, such as nitrogen, comprising a small amount of hydrogen. The nitrogen typically contains initially about 2.0% by volume of $H_2$. In this case, the temperature is raised, for example, from 100 to 235° C. over a period of 16 hours. Thereafter, the hydrogen content is increased, and reduction is effected, for example, with 20% by volume of $H_2$ (remainder $N_2$) within the temperature range from 235 to 270° C. over a period of 3 hours. The reductive treatment can be completed with 99.9% $H_2$ at from 270° C. to 300° C. over a period of about 3 hours. Typically, activation is effected with a superficial velocity of from about 3000 to 4000 liters of reduction gas per hour and liter of catalyst.

In the reduced state, the size of the copper crystals is preferably from about 4 to 12 nm, preferably from 5 to 7 nm.

The inventive catalyst is suitable especially for use in methanol synthesis. The invention therefore also provides for the use of the above-described catalyst for synthesizing methanol from CO, $CO_2$ and $H_2$. The synthesis is typically performed at a temperature of from about 200 to 320° C., preferably at from 210° C. to 280° C., at a pressure of from about 40 to 150 bar, preferably at from about 60 to 100 bar, and at a superficial velocity of from about 2000 to 22 000, preferably from 8000 to 12 000, liters of synthesis gas per hour and liter of catalyst, and the synthesis gas may contain from about 5 to 25% by volume, preferably from 6 to 12% by volume, of CO, from about 4 to 10% by volume of $CO_2$, from about 10 to 30% by volume of $N_2$ plus $CH_4$ (inert gases) and, as the remainder, $H_2$.

The inventive catalyst is also suitable for use in methanol reformation and in the low-temperature conversion of carbon monoxide to carbon dioxide. The latter reaction, also referred to as the low-temperature shift (LTS), is effected at temperatures in the range from about 175 to 250° C., preferably from 205 to 215° C., and steam/gas ratios in the range from about 0.4 to 1.5 (1 (STP)/1 (STP)). Typical feed gas mixtures contain about 3% by volume of CO, 17% by volume of $CO_2$, 2% by volume of $N_2$ and 78% by volume of $H_2$, which are passed through the reactor with superficial velocities of from about 2000 to 12 000 l of dry gas (i.e. without water) per liter of catalyst and hour. Good catalysts achieve, at a superficial velocity of 11 200 $h^{-1}$ and a ratio of steam to gas of about 1.5, CO conversions of from 70 to 85%.

The invention is illustrated in detail hereinafter with reference to examples.

EXAMPLE

(a) Preparation of the Copper Solution 5054 g of a suspension of $Cu(OH)_2.CuCO_3$ (Cu content: 27.7% by weight, corresponding to 1400 g of Cu) are dispersed in a 10 l beaker and admixed in portions with a total of 2399 ml of 85% formic acid (D=1.1856 g/cm³) until the $CO_2$ evolution has ended. The copper solution has a pH of 2.35 and a temperature of 55° C.

(b) Preparation of the Cu/Zn Solution

Precursor to First Solution

In a 5 l beaker, a ZnO dispersion is prepared from 781 g of ZnO and 4000 ml of $H_2O$. The suspension is combined with the copper solution obtained in (a). With continued dispersion, a further 890 ml of formic acid and 33.6 l of demineralized water are added in portions. The blue, initially still slightly opal solution is stirred until it is completely clear.

(c) Preparation of the Sodium Carbonate Solution

Second Solution 24 000 ml of $Na_2CO_3$ solution which has a concentration of approx. 180 g of $CO_3$/100 ml are prepared, and the solution is heated to 70° C.

(d) Preparation of the Aluminum Solution I

A 5 l stirred apparatus provided with a cooling device is initially charged with 2193 ml of demineralized water and 246.7 g of $NaAlO_2$ are added. The solution is heated to a temperature of not more than 30° C., and then 350 ml of formic acid are added in portions. The milky solution has a pH of approx. 4.0.

(e) Preparation of the Aluminum Solution II

A stirred apparatus provided with a cooling device is initially charged with 2193 ml of water, and 246.7 g of $NaAlO_2$ are added in portions. It is ensured that the temperature of the solution does not exceed 30° C. The mixture is stirred until a clear solution is obtained.

(f) Precipitation

The solution obtained in (b) is transferred to a first reservoir tank of a mixing apparatus. Subsequently, the aluminum solution I obtained in (d) is introduced into the tank and stirred there at room temperature until the combined solutions are completely clear. Water can optionally be added in order to eliminate the opalescence of the solution. Before the start of precipitation, the solution is heated to 70° C. Approx. 30 minutes before the start of precipitation, the aluminum solution II obtained in (e) is transferred into the tank, which forms a milky, white-bluish suspension.

The $Na_2CO_3$ solution obtained in (c) is introduced into a second reservoir tank and heated to 70° C.

The solutions present in the first and second tank are simultaneously fed to a mixing apparatus and, after a residence time of about 20 s, pass from there into an overflow vessel. The pumping rates are adjusted such that the pH during the precipitation is about 6.5±0.1. From the mixing apparatus, the mixture passes into an overflow vessel. From the overflow vessel, the suspension formed passes into an aging vessel, where it is kept at approx. 65° C. with stirring. The precipitation has ended after approx. 35 minutes. Subsequently, the unit is flushed with approx. 600 ml of demineralized water and the temperature in the aging vessel is increased to 70° C. After the flushing operation has ended, the suspension is aged with stirring. The commencement of the aging is defined by the end of the flushing operation. The aging times employed in the examples are specified in table 2.

After the aging has ended, the suspension is filtered and washed with demineralized water until the residual content of sodium in the filtercake has fallen to less than 350 ppm, and the resulting solid is dried by spray-drying using a one-substance nozzle in countercurrent. The feed established is a suspension with a dry substance content of 30% by weight. The heating gas entrance temperature is 330-350° C., the product exit temperature 110-120° C. The dried powder is subsequently calcined at about 320° C. for 50 minutes either in porcelain dishes in a staged oven or in a batchwise laboratory rotary tube oven.

(g) Treatment of the Wastewater

The wastewater obtained in the filtration and the washing is treated by adding hydrogen peroxide, the pH being kept between 5 and 6.5 with sulfuric acid and the temperature of the wastewater at approx. 70° C. The formate concentration of the wastewater is adjusted to values between 2.8% by weight and 0.09% by weight. The selectivity, defined as mol of formate converted/mol of hydrogen peroxide used, is approx. 60%.

Comparative Example

(a) Preparation of a Copper/Zinc Nitrate Solution 781.25 g of zinc oxide are added to 9.79 kg of a copper nitrate solution which contains 1400 g of copper. 2077 g of nitric acid (58%) are then added and the mixture is stirred until the solids have dissolved completely.

(b) Preparation of an Aluminum Nitrate Solution 246.7 g of $Na_2AlO_2$ are dissolved in 1.5 l of demineralized water. 1365 g of nitric acid (58%) are then added and the mixture is stirred until a clear solution is obtained. The aluminum nitrate solution obtained is added to the copper/zinc nitrate solution and the Cu/Zn/Al solution is heated to 60° C.

(c) Preparation of the Aluminum Sol 246.7 g of $Na_2AlO_2$ are dissolved in 1.5 l of demineralized water with stirring over 30 minutes. The resulting solution is added to the Cu/Zn/Al solution and the mixture is heated to 60° C.

(d) Precipitation

The mixture obtained in (c) is introduced into the first reservoir tank of a mixing apparatus. 25 l of an aqueous solution which contains 172 g of $Na_2CO_3$ per liter are introduced into the second reservoir tank of the mixing apparatus. The two solutions are pumped simultaneously into a mixing vessel and the mixture is passed from there into an aging vessel.

After the end of precipitation, the mixing vessel is flushed with demineralized water, the temperature in the aging vessel is increased to 70° C. and the precipitate is aged for 1 or 4 hours. After the aging has ended, the suspension is filtered and washed with demineralized water until the residual content of sodium in the filtercake has fallen to less than 350 ppm, and the resulting solid is dried in countercurrent by spray-drying using a one-substance nozzle. The heating gas entrance temperature is 330-350° C., the product exit temperature 110-120° C. The dried powder is subsequently calcined at about 320° C. for 50 minutes either in porcelain dishes in a staged oven or in a batchwise laboratory rotary tube oven.

The precipitation examples performed and the calcination conditions employed thereafter are compiled in tables 2a+b. Likewise included in these tables are the chemical compositions and the physical parameters of the resulting oxidic catalyst precursors.

The determination of the physical parameters is undertaken in the following manner:

Determination of the Cu Crystal Size:

The size of the Cu crystals is determined by means of X-ray powder diffractometry (XRD). The Cu (111) reflection in the region of ~43.3° (2☐) is analyzed. The half-height width and the integral intensity of the reflection are calculated with the pseudo-Voigt function. The Cu crystal size is calculated with the aid of the Scherrer function on the basis of the calculated half-height width.

For preparation for the X-ray determination of the crystal size, the oxidic catalysts are reduced as follows:

2-5 g of tablets having a size of 6×4 mm are heated in a tube reactor from room temperature to a maximum temperature at a heating rate of 2° C./min with a reduction gas (98% $N_2$, 2% $H_2$). Catalysts which have been prepared from the formates are heated to a maximum temperature of 80-120° C. Catalysts which have been prepared using the nitrates are first heated to 175° C. overnight. Subsequently, within less than 2 hours, the maximum temperature is established: 180° C. for catalysts from a) the formate/carbonate route; 240° C. for catalysts from b) the nitrate/carbonate route. While maintaining the maximum temperature, the hydrogen content of the reduction gas is finally increased to 100% within one hour and then the sample is reduced for a further 3 hours.

Determination of the Specific Surface Area

The BET surface area is determined by the one-point nitrogen method on the pulverulent oxidic catalyst and on 6×4 mm tablets on the basis of DIN 66132.

Determination of the Ignition Loss

When the ignition loss is to be determined on tablets, they are first ground to a powder. The sample to be determined is weighed into a weighed porcelain crucible which had been heated beforehand at 600° C. in a muffle furnace for 3 hours and then cooled to room temperature in a desiccator. The crucible is heated to 600° C. in a muffle furnace for 3 hours and then cooled to room temperature in a desiccator. The cooled crucible is weighed again and the ignition loss at 600° C. is determined from the difference.

Determination of the Side Crushing Strength

The side crushing strength is determined to DIN EN 1094-5, 1995-09 edition, feuerfeste Erzeugnisse für Isolationszwecke [Refractory products for insulation purposes]—part 5: Bestimmung der Kaltdruckfestigkeit geformter Erzeugnisse [Determination of the cold compressive strength of molded products]. The determination is performed with a commercial instrument such as Schleuninger 6-D or ERWEKA TBH 310 MD according to the instrument manufacturer's instructions.

For a representative sample amount of 100 tablets, the pressures acting on their cylinder layer in the bursting operation are determined and evaluated with the instrument's own statistics program for mean, standard deviation and minimum and maximum hardness. The distribution of the tablet hardness (N) is shown in graphic form.

Determination of the Pore Volume

The pore volume is determined by the mercury intrusion method on the basis of DIN 66133 on the pulverulent oxidic catalysts and on 6×4 mm tablets.

Determination of the Formate Content

Approx. 10 to 20 g of the calcined catalyst powder are taken up in 25+x ml of $H_2SO_4$ (25%) and dissolved with heating to approx. 70° C. in a 300 ml Erlenmeyer flask. The amount x ml of $H_2SO_4$ (25%) is determined by the minimum amount of sulfuric acid which may be additionally required to achieve complete dissolution of the amount weighed in. The mixture is made up to approx. 100 ml with distilled water. Addition of approx. 2.5 to 25 ml of NaOH (30%) adjusts the solution to a pH of from 8 to 10. The solution is then heated to 70° C. for at least a further 5 minutes. Subsequently, 20 ml of $KMnO_4$ solution (0.2 N) are added and the solution is heated to gentle boiling for at least 30 min. The hot solution is acidified with $H_2SO_4$ (25-50 ml) and 20 ml of oxalic acid (0.2 N) are added in order to reduce manganese dioxide and excess $KMnO_4$ to $Mn^{2+}$. The oxalic acid solution added has to correspond exactly to the oxidation equivalents of the permanganate solution in its content of reduction equivalents. The clear solution is ultimately titrated with 0.2 N KMnO$_4$ until a slight pink coloration is observed.

Calculation:

Every ml of 0.2 N KMnO$_4$ solution consumed corresponds to 4.5 mg of formate. The percentage content of formate in the sample is found to be:

[% formate]=[(ml of 0.2 N KMnO$_4$ solution consumed)×(4.5 mg of formate/ml of 0.2 N KMnO$_4$ solution)×100)/(weight of sample in mg)]

The method affords verified results for formate concentrations in the solution to be titrated between 0.08 and 0.5% by weight with deviations of <+8%. These deviations can be reduced to +/−2% in the case of use of a 0.02 N permanganate solution. Owing to the dependence of the method accuracy on the formate concentration which is unknown per se, it may be necessary to align the sample weight first to an expected value in order to, after the first result is present, repeat the titration with an adjusted sample weight, which then gives rise to formate concentrations within the abovementioned range for the solution to be titrated.

The formate contents of the samples from examples 3 and 5 are reported in table 1.

TABLE 1

Formate content of calcined catalysts (values t.q. = not based on ignition loss)

| Example | Formate content |
|---------|-----------------|
| 3 | 1.3% |
| 5 | 1.1% |

The physical properties of the catalysts prepared are reported in table 2. Table 2a is based on the pulverulent catalysts, while the values from table 2b are based on catalysts which have been compressed to tablets having the dimensions of 6×4 mm.

TABLE 2a

Physical data of the oxidic catalyst powders prepared

| No. | Aging (h) | Staged oven calcination, bed height 5 mm (° C./min) | Cu (%) | Zn (%) | Al (%) | Specific surface area[3] (m$^2$/g) | PSD[4] D$_{50}$ (μm) | Ignition loss (600° C.) | Process[7] |
|-----|-----------|------------------------------------------------------|--------|--------|--------|------------------------------------|----------------------|-------------------------|------------|
| 0[1] |          |                                                      | 48.3   | 22.1   | 4.9    |                                    |                      | 9.4                     | N          |
| 1[2] | 1         | 320/50                                               | 50.1   | 21.5   | 5.3    | 126.0                              | 23.3                 | 6.9                     | N          |
| 2[2] | 4         | 320/50                                               | 50.1   | 21.5   | 5.3    | 117.0                              | 21.2                 | 4.7                     | N          |
| 3[2] | 1         | 320/50                                               | 49.6   | 21.8   | 5.1    | 134.0                              | 20.3                 | 15.2                    | F          |
| 4[2] | 1         | 350/100                                              | 49.6   | 21.8   | 5.1    | 129.0                              | 20.2                 | 6.8                     | F          |
| 5[2] | 4         | 320/50                                               | 49.2   | 22.4   | 5.0    | 130.0                              | 19.4                 | 14.7                    | F          |
| 6[2] | 4         | 350/100                                              | 49.2   | 22.4   | 5.0    | 123.0                              | 18.8                 | 6.4                     | F          |
| 7[8] | 1         | 320/105                                              | 49.5   | 18.6   | 5.0    | 102.0                              | 15.6                 | 7.2                     | F          |
| 8[8] | 4         | 320/105                                              | 49.5   | 18.6   | 5.0    | 113.0                              | 14.7                 | 8.2                     | F          |

[1]Industrial standard
[2]Prepared using a type A mixing tube
[3]BET
[4]Particle size distribution
[7]N = nitrate route; F = formate route
[8]Prepared using a type B mixing tube TABLE 2b Physical data of the tablets prepared from the catalysts

| No. | Specific surface area[3] (m²/g) | SCS (N)[5] | Large Cu crystals (Å) | PV[6] R = 3.75 – 7500 nm (mm³/g) | PV[7] R = 3.75 – 7.0 nm (mm³/g) | PV[7]/PV[6] (%) | PV[7] (sample)/ (standard) % |
|---|---|---|---|---|---|---|---|
| 0 | 80.3 | 155.0 | 75.0 | 268.8 | 82.8 | 30.8 | 100 |
| 1 | 93.0 | 159.8 | 67.8 | 256.7 | 128.3 | 50.0 | 155.0 |
| 2 | 99.0 | 157.0 | 63.4 | 283.9 | 136.0 | 47.9 | 164.3 |
| 3 | 115.0 | 157.9 | 62.7 | 425.2 | 159.0 | 37.4 | 192.1 |
| 4 | 104.0 | 176.3 | 50.9 | 340.2 | 140.6 | 41.3 | 169.9 |
| 5 | 111.0 | 159.1 | 59.9 | 435.8 | 149.5 | 34.3 | 180.6 |
| 6 | 99.0 | 185.1 | 56.6 | 281.1 | 150.8 | 53.6 | 182.2 |
| 7 | 91.0 | 213.9 | 67.3 | 277.1 | 92.5 | 33.4 | 111.8 |
| 8 | 99.0 | 202.7 | 55.4 | 286.7 | 102.9 | 35.9 | 124.3 |

[5]Side crushing strength
[6,7]Pore volume determined by the Hg intrusion process at 2000 bar Methanol Activity Tests The oxidized tablets are quartered, and a screen fraction of from 2.5 to 3.5 mm is filled into a crude reactor and, after activation, subjected to a standardized activity test with periodically alternating temperatures. In the evaluation, the weight-time yields (WTY) in kg (methanol)/(kg (catalyst)×h) are determined as the mean for one period at constant temperature in each case. In a test reactor system consisting of 6-16 individual tubes, in a test tube, the catalyst C79-7 from Süd-Chemie AG, Munich, Germany is used as a standard and the WTY determined for the other samples is in each case determined relative to the value for the standard. This process has the advantage that small variations, for example, in the synthesis gas composition are the same for all specimens, and the results from different test runs can thus be compared with one another.

By-products are determined with the aid of gas chromatography analysis of condensate samples to which an internal standard has been added in each case. The values determined are likewise reported relative to the values which are obtained for the standard.

The results of the methanol activity test are listed in table 3.

TABLE 3b

Experiment time (time on stream "TOS")

| Index | Time (h) | Index | Time (h) | Index | Time (h) | Index | Time (h) |
|---|---|---|---|---|---|---|---|
| 1 | 0-96 | 2 | 96-144 | 3 | 144-192 | 4 | 192-240 |
| 5 | 0-75 | 6 | 75-171 | 7 | 171-243 | 8 | 243-339 |
| 9 | 0-96 | 10 | 96-186 | 11 | 186-231 | | |

The invention claimed is:

1. A process for preparing Cu/Zn/Al catalysts, comprising
preparing a first aqueous solution which comprises copper formate and zinc formate,
preparing a second solution which comprises a precipitation reagent,
wherein the first solution and/or the second solution further comprises an aluminum hydroxide sol/gel mixture,
combining the first solution and the second solution to obtain a precipitate,

TABLE 3

Relative weight-time yields based on standard catalyst

| | WTY | | | | Total by-products | | | | Ethanol by-product | | | |
|---|---|---|---|---|---|---|---|---|---|---|---|---|
| No. | 250° C. | 230° C. | 210° C. | 250° C. | 250° C. | 230° C. | 210° C. | 250° C. | 250° C. | 230° C. | 210° C. | 250° C. |
| 0 | 100.0[1] | 100.0[2] | 100.0[3] | 100.0[4] | 100.0[1] | 100.0[2] | 100.0[3] | 100.0[4] | 100.0[1] | 100.0[2] | 100.0[3] | 100.0[4] |
| 1 | 92.2[1] | 86.2[2] | 82.6[3] | 93.0[4] | 89[1] | 86[2] | 87[3] | 108[4] | 92[1] | 97[2] | 99[3] | 98[4] |
| 2 | 96.0[1] | 94.2[2] | 93.5[3] | 97.6[4] | 97[1] | 93[2] | 86[3] | 111[4] | 96[1] | 91[2] | 68[3] | 104[4] |
| 3 | 103[5] | 96[6] | 91[7] | 99[8] | 99[5] | 95[6] | 115[7] | 97[8] | 98[5] | 96[6] | 163[7] | 93[8] |
| 4 | 106[5] | 102[6] | 96[7] | 102[8] | 101[5] | 104[6] | 120[7] | 109[8] | 111[5] | 118[6] | 235[7] | 109[8] |
| 5 | 102.4[1] | 96.9[2] | 97.1[3] | 101.0[4] | 103[1] | 89[2] | 95[3] | 114[4] | 102[1] | 89[2] | 61[3] | 99[4] |
| 6 | 99.2[1] | 99.0[2] | 100.9[3] | 99.1[4] | 113[1] | 92[2] | 78[3] | 109[4] | 107[1] | 72[2] | 34[3] | 94[4] |
| 7 | 96.4[9] | | 78.9[10] | 92.2[11] | 102[9] | | 111[10] | 109[11] | 103[9] | | 194[10] | 107[11] |
| 8 | 103.5[9] | | 100.5[10] | 102.0[11] | 109[9] | | 98[10] | 117[11] | 119[9] | | 128[10] | 119[11] | removing the precipitate from the combination of solutions thereby producing wastewater,
washing the precipitate until an alkali metal content, based on the precipitate after being formed as a catalyst is calcined at 600° C., of less than 500 ppm is attained, and
drying the precipitate.

2. The process as claimed in claim 1, characterized in that the first solution is prepared by
preparing an aqueous copper formate solution by dissolving a copper salt without residue by use of formic acid,
preparing an aqueous dispersion or solution of a zinc salt,
preparing an aqueous aluminum salt solution, and
combining the copper formate solution, the dispersion or solution of the zinc salt and the aluminum salt solution.

3. The process as claimed in claim 2, wherein the copper formate solution has a pH of less than 3.

4. The process as claimed in claim 2, wherein the solution or dispersion of the zinc salt is combined with the copper formate solution to give a copper/zinc solution, wherein the resulting copper/zinc solution has a pH in the range from 3.0 to 4.0, and wherein the aluminum salt solution is added to the copper/zinc solution.

5. The process as claimed in claim 4, wherein the aluminum salt solution is added in several part-solutions, at least a first portion of the aluminum salt solution being prepared by dissolving at least a first part of the aluminum salt in water with an addition of formic acid.

6. The process as claimed in claim 5, wherein a second portion of the aluminum salt solution is prepared by dissolving a second portion of the aluminum salt in water and adding a first portion of the aluminum salt solution and the second portion of the aluminum salt solution, to the copper/zinc solution.

7. The process as claimed in claim 6, characterized in that the aqueous aluminum salt solution, the first portion of the aluminum salt solution and/or the second portion of the aluminum salt solution, before precipitation, is/are heated to temperatures of not more than 40° C.

8. The process as claimed in claim 1, wherein, during the precipitation step, a pH in the range from 3.5 to 7.5, is maintained.

9. The process as claimed in claim 2, characterized in that the copper salt is selected from the group consisting of CuO, $Cu(OH)_2$, $Cu(OH)_2 \cdot CuCO_3$ and mixtures thereof.

10. The process as claimed in claim 2, characterized in that the zinc salt comprises ZnO.

11. The process as claimed in claim 1 further comprising a precipitation reagent comprising an alkali metal base.

12. The process as claimed in claim 1 further comprising a precipitation reagent comprising hydrogen peroxide.

13. The process as claimed in claim 1, characterized in that the precipitate is aged after the precipitation.

14. The process as claimed in claim 13, characterized in that the aging is performed over a period of from 10 minutes to 10 hours.

15. The process as claimed in claim 13, characterized in that the aging is effected at a temperature of more than 60° C.

16. The process as claimed in claim 1, characterized in that the precipitation step is performed as a continuous precipitation.

17. The process as claimed in claim 1, characterized in that the first solution comprises copper and zinc in a ratio which is selected between 1:99 and 99:1.

18. The process as claimed in claim 1, characterized in that the precipitate is calcined after drying.

19. The process as claimed in claim 18, wherein the precipitate is calcined at temperatures in the range of 140-1000° C., for a period of at least 0.1 second.

20. The process as claimed in claim 1, characterized in that the wastewater comprises formate ions and the wastewater is subjected to an oxidative treatment which oxidizes the formate ions essentially to carbonate, hydrogencarbonate, carbon dioxide and water.

21. The process as claimed in claim 20, characterized in that hydrogen peroxide is added to the wastewater for the oxidative treatment.

22. The process as claimed in claim 20, characterized in that the oxidative treatment of the wastewater occurs before the removal of the precipitate.

23. The process as claimed in claim 20, characterized in that the oxidative treatment comprises a biological treatment of the wastewater.

24. A Cu/Zn/Al catalyst which has been obtained by the process as claimed in claim 1 and which has a formate content, based on the oxidic catalyst, of less than 5%.

25. The catalyst as claimed in claim 24, characterized in that the proportion of mesopores of the catalyst having a radius from 3.75 to 7.0 nm in the total pore volume is more than 30%.

26. The catalyst as claimed in claim 24, characterized in that the proportion of copper, calculated as copper oxide and based on the weight of the oxidic catalyst, is between 55 and 69% by weight.

27. The catalyst as claimed in claim 24, characterized in that the proportion of zinc, calculated as zinc oxide and based on the weight of the oxidic catalyst, is between 20 and 33% by weight.

28. The catalyst as claimed in claim 24, characterized in that the proportion of aluminum, calculated as aluminum oxide and based on the weight of the oxidic catalyst, is between 5 and 20% by weight.

29. The catalyst as claimed in claim 24, characterized in that the oxidic catalyst has a content of alkali metal ions of less than 500 ppm.

30. A methanol synthesis reaction comprising converting CO, $CO_2$ and $H_2$ to methanol utilizing the catalyst as claimed in claim 24.

31. A reformation of methanol reaction utilizing the catalyst as claimed in claim 24.

32. A low-temperature conversion of carbon monoxide to carbon dioxide comprising reacting carbon monoxide and water over the catalyst of claim 24 to produce carbon dioxide at a temperature from 175 to 250° C.

* * * * *

UNITED STATES PATENT AND TRADEMARK OFFICE
CERTIFICATE OF CORRECTION

| | | |
|---|---|---|
| PATENT NO. | : 7,820,128 B2 | Page 1 of 1 |
| APPLICATION NO. | : 11/911581 | |
| DATED | : October 26, 2010 | |
| INVENTOR(S) | : Siegfried Polier et al. | |

It is certified that error appears in the above-identified patent and that said Letters Patent is hereby corrected as shown below:

Title Page, and Col. 1

Title, that portion of the title reading "CU/ZN/A1" should read --CU/ZN/AL--.

Signed and Sealed this
Fifth Day of July, 2011

David J. Kappos
*Director of the United States Patent and Trademark Office*